United States Patent [19]

Beguin

[11] 4,221,795

[45] Sep. 9, 1980

[54] PYRIDINE DERIVATIVE, ITS PREPARATION AND USE

[75] Inventor: Alain Beguin, Meudon, France

[73] Assignee: Societe Civile de Recherches et d'Applications Scientifiques, France

[21] Appl. No.: 963,383

[22] Filed: Nov. 24, 1978

[30] Foreign Application Priority Data

Nov. 25, 1977 [GB] United Kingdom ............... 49199/77

[51] Int. Cl.$^2$ ........................................... C07D 471/04
[52] U.S. Cl. .................................... 424/256; 542/454; 542/466; 542/439
[58] Field of Search ................. 542/454, 466; 424/256

[56] References Cited

PUBLICATIONS

Chemical Abstracts, 9th Collective Index, p. 16920 CS.
Merck, Chem. Abstracts, 1961, col. 10478(a).
Descamps et al., Chem. Abstracts, 59(1963) col. 1607b.

*Primary Examiner*—Arthur P. Demers
*Attorney, Agent, or Firm*—Eyre, Mann, Lucas & Just

[57] ABSTRACT

A pyridine derivative having the formula 1,3-dihydro-3-(3',4',5'-trimethoxy-styryl)-6-methyl-7-hydroxy-furo-[3,4,c]pyridine and therapeutically acceptable salts thereof are disclosed. Also disclosed is a process for the preparation of the compound. The compounds are therapeutically useful for a stabilizing effect on the red blood corpuscles and as selective diuretics.

3 Claims, No Drawings

PYRIDINE DERIVATIVE, ITS PREPARATION AND USE

This invention relates to a pyridine derivative, to a process for its preparation and to therapeutic compositions containing it.

The new compound according to this invention is 1,3-dihydro-3-(3',4',5'-trimethoxy-styryl)-6-methyl-5-hydroxy-furo-[3,4,c] pyridine which has the formula: I, and the therapeutically acceptable salts thereof.

The empirical formula of the above compound is $C_{19}H_{21}NO_5$ and its molecular weight is 343. It is of interest because of its activity in the field of the protection of kidney and diuresis. It has shown a low toxicity: per os LD 50 on mice is over 2.4 g/kg.

The invention also provides a process for the preparation of the above compound which comprises reducing, by sodium borohydride, the keton II, into the corresponding secondary alcohol (reaction scheme 5) followed by treatment of the product with an alcoholic solution of formic and hydrochloric acids to break the isopropylidene bridge (reaction scheme 6), and induce an internal condensation to yield the product of the invention.

The reaction (schemes 1 to 3) show one possible way of preparing the isopropylidene blocked pyridine derivative which is used in reaction 4 for the preparation of the complex keton II. This step comprises treating 2-methyl-3-hydroxy-4-hydroxymethyl-5-acetyl-pyridine in which the 3- and 4-hydroxy groups are blocked with an isopropylidene bridge, in the presence of a strong base, with 3,4,5-trimethoxybenzaldehyde in solution in aqueous alcohol at or slightly above room temperature. The keton is thus treated according to the reaction sequence 5+6 describing the process of the present invention.

The starting material for reaction 1, pyridoxine in which the 3- and 4-hydroxy groups are blocked with an isopropylidene bridge, may be obtained as described in the previous American Pat. No. 3,717,636 of Feb. 20, 1973.

Finally, the invention relates also to therapeutical compositions wherein an active ingredient is the compound I or any of its therapeutically acceptable salts.

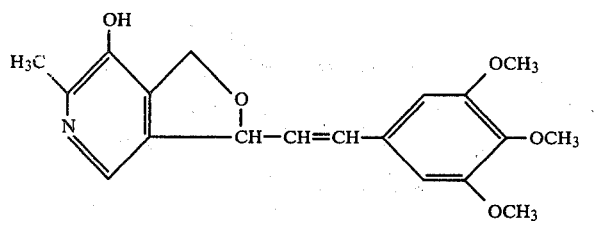

I

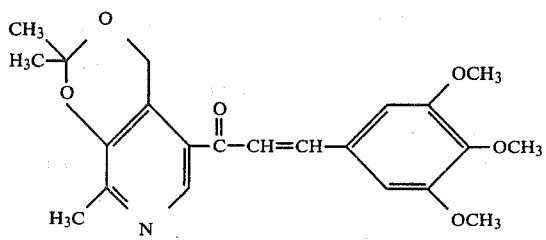

II

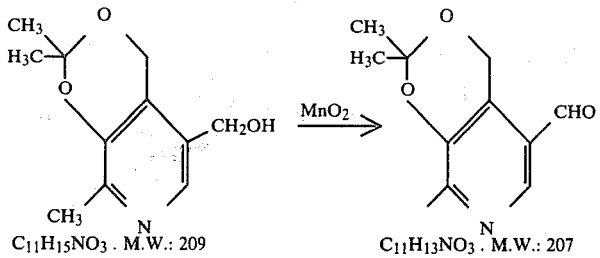

1.

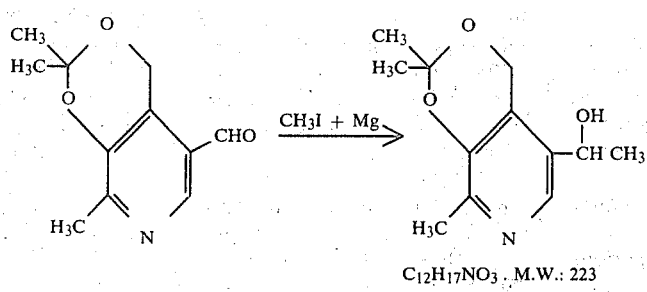

2.

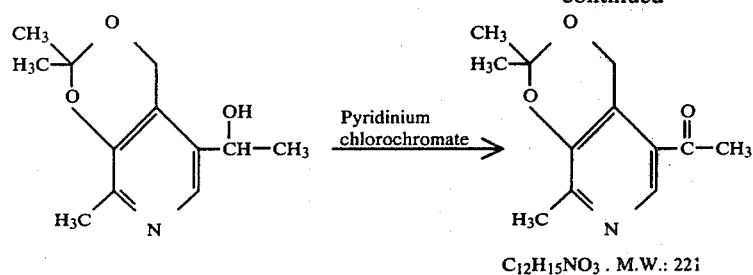

-continued

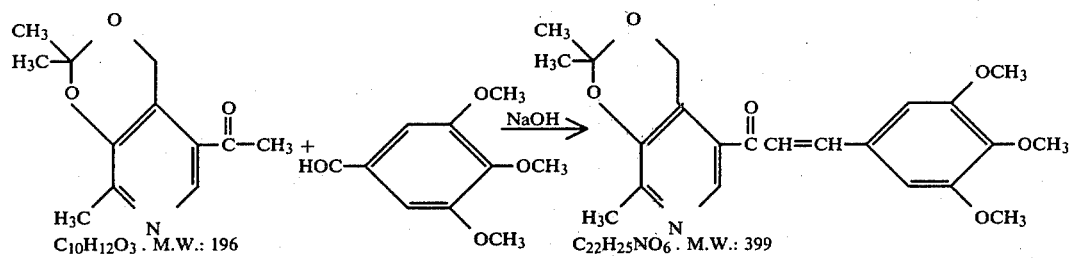

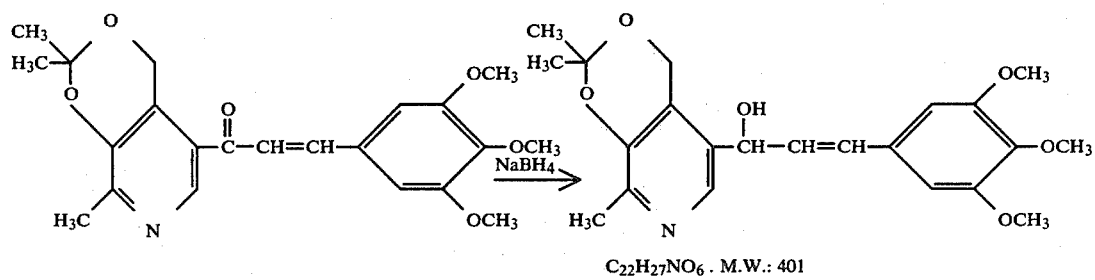

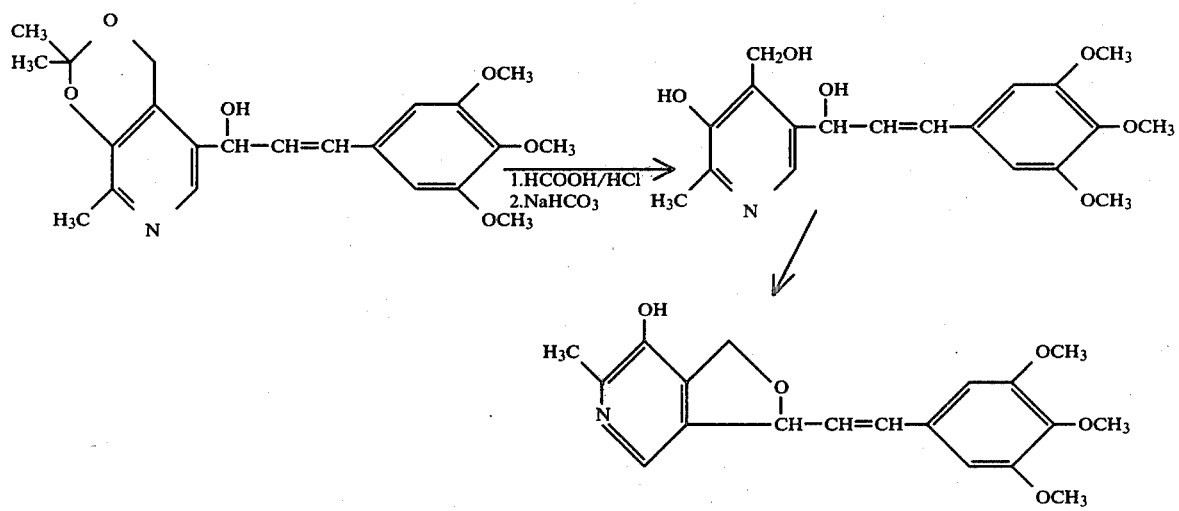

The following example illustrates this invention.

EXAMPLE

Pyridoxine in which the 3- and 4-hydroxy groups are blocked by an isopropylidene bridge was obtained as hereabove indicated and was treated conventionally by $MnO_2$ to give the corresponding 5-aldehyde. This compound, after separation and purification, was treated with methyl iodide in the presence of magnesium to give the corresponding 5-(2'-hydroxyethyl) compound. This compound in turn was transformed into the corresponding 5-acetyl derivative by treatment with pyridinium chlorochromate and dry sodium acetate, in solution in dry methylene dichloride. These reactions are well known and do not need further description. The following steps will now be described in more detail.

In a two-liter reactor there were poured 221 g. (1 mol) of the 3,4-isopropylidene blocked 2-methyl 3-hydroxy-4-hydroxymethyl-5-acetylpyridine, 42.8 g. (1.1 mol) of sodium hydroxide, 0.5 liter of water and 0.25 liter of ethanol. The reaction proceeded as in reaction 4 above. The mixture was stirred at room temperature and there were slowly added, whilst stirring and at about 40° C., 196 g. (1 mol) of trimethoxybenzaldehyde. Stirring was maintained for 4 hours at the same temperature. There was then added 0.75 liter of water, and a precipitate formed. Stirring was maintained for another hour. The precipitate was separated, washed with water, then with ethanol, recrystallized from methanol and dried. Yield 335 g. (84%).

300 g. (0.75 mol) of this product were treated according to reaction scheme 5 above at 0° C. to 5° C., in a 5-liter reactor containing 2.5 liters of methanol, with 88.5 g. (2.34 mol) of NaBH4 which were slowly added whilst stirring. A precipitate appeared and 3 hours after the end of the addition, there was added, dropwise, a sufficient amount of acetic acid to reach pH6. The precipitate was separated, washed and recrystallized from a 50/50 water-ethanol mixture. There was obtained 235 g. (78%) of the secondary alcohol.

ratio Na/K is over 200%, either for the compound itself or its pharmaceutically acceptable salts. Similar results are found on the same experimentation on the mice.

3. The protection in vivo has been evidenced on rats having received high doses of glafenine or tetracycline which are known to provoke alteration or necrosis in the kidney. Antagonist action of the compound of the invention has been measured by the variation of plasmatic urea and creatinine values compared with non-treated animals and with animals treated by glafenine or tetracycline; the variation of hematocrite and of the diuresis were measured at the same time.

For therapeutic use, the dosage unit contains from 0.020 to 0.5 g. of the active compound.

| Tested Concentration mM | PHENYLBUTAZONE | | Compound | | PHENYLBUTAZONE | | Compound | |
|---|---|---|---|---|---|---|---|---|
| | OD | % of PROTECTION | OD | % of PROTECTION | OD | % of PROTECTION | OD | % of PROTECTION |
| 0 | 561 | — | 589 | — | 1290 | — | 1410 | — |
| 0.1 | — | — | — | — | 826 | 35 | 977 | 23 |
| 0.2 | 380 | 36 | 471 | 20 | 641 | 49 | 979 | 23 |
| 0.5 | 352 | 41 | 381 | 36 | 499 | 61 | 841 | 33 |
| 1 | 386 | 35 | 361 | 39 | 434 | 66 | 825 | 35 |
| 5 | 232 | 61 | 276 | 53 | 272 | 79 | 577 | 54 |
| 10 | 149 | 75 | 247 | 58 | Hemolized | — | 805 | 36 |
| 20 | Hemolized | — | 228 | 61 | Hemolized | — | 938 | 35 |

For the final step, (reaction scheme 6 above), 214 g. (0.534 mol) of the compound thus obtained were treated in a reactor by 0.7 liter of HCl (1.9 N) and 0.87 liter of 1% formic acid in 1.5 liters of ethanol over a water bath for 30 minutes. The solution was then filtered, evaporated and retreated with diethyl ether, filtered, dried and finally dissolved in 2 liters of water and treated by NaHCO3 (pH 7-8) with stirring. The precipitate obtained was separated, washed with water and recrystallized from methanol.

Yield 171 g. (87%) of a product, the analysis of which showed a good correspondence with the formula $C_{19}H_{21}NO_5$. The structure of the product was confirmed by nuclear magnetic resonance.

The interest of the compound of the present invention will be understood from the reports of the following pharmacological experimentations:

1. Stabilization on membrane in vitro.

In this experimentation, the stabilizing effect has been researched on the red blood corpuscle membrane of rabbit, by determination of the hemolysis rate during the incubation in hypotonic conditions (phosphate buffer 10 mM, pH: 7.4, -Na Cl 5.5 g/liter) at 53° C. The tested products are added to the incubation environment at various concentrations and the hemolysis rate is compared to a control. This experimentation is carried comparatively with Phenyl-butazone, known to have a similar highly favourable action. The results are reported in the following table in which OD means average optical density on 3 assays.

2. Variation of diuresis on normal animals.

The compound of the present invention induces a selective diuresis which has been evidenced on rats and mice; these experimentations have shown a very favourable rate of elimination of sodium compared with potassium, which is of high importance in diuresis. For instance, compared with control animal, on the rat, the

I claim:

1. Pyridine derivative of the formula:

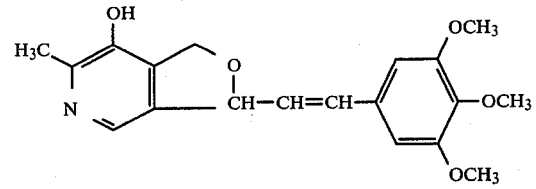

and therapeutically acceptable salts thereof.

2. Preparation process of the compound of claim 1 comprising reducing, by sodium borohydride, the ketonic compound

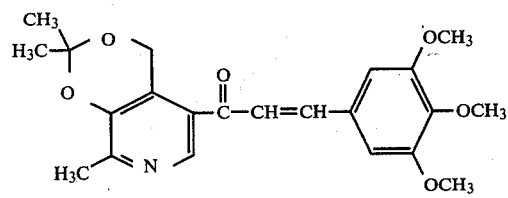

to the corresponding secondary alcohol, then breaking the isopropylidene bridge on the pyridine ring by the action of an alcoholic solution of formic and hydrochloric acids and finally treating by mono sodium carbonate.

3. A therapeutic composition comprising as an active agent, the compound of claim 1 or a therapeutically acceptable salt thereof dosed at 0.020 to 0.5 g. per dosage unit together with a pharmaceutically acceptable carrier therefor.

* * * * *

UNITED STATES PATENT AND TRADEMARK OFFICE
CERTIFICATE OF CORRECTION

PATENT NO. : 4,221,795
DATED : September 9, 1980
INVENTOR(S) : Alain Beguin

It is certified that error appears in the above–identified patent and that said Letters Patent are hereby corrected as shown below:

Column 1, lines 9-10: change "1,3-dihydro -3-(3', 4',5'-trimethoxy-styryl)-6-methyl-5-hydroxy-furo-[3,4,c] pyridine" to --1,3-dihydro-3-(3',4',5'-trimethoxy-styryl)-6-methyl-7-hydroxy-furo-[3,4,c] pyridine--.

Signed and Sealed this

Seventeenth Day of March 1981

[SEAL]

Attest:

RENE D. TEGTMEYER

Attesting Officer      Acting Commissioner of Patents and Trademarks